(12) United States Patent
Chong

(10) Patent No.: US 9,560,972 B2
(45) Date of Patent: Feb. 7, 2017

(54) SELF-OPERATED HEALTH MONITORING DEVICE

(71) Applicant: SANTEC CORPORATION, Komaki, Aichi (JP)

(72) Inventor: Changho Chong, Los Altos, CA (US)

(73) Assignee: SANTEC CORPORATION, Komaki, Aichi (JP)

( * ) Notice: Subject to any disclaimer, the term of this patent is extended or adjusted under 35 U.S.C. 154(b) by 33 days.

(21) Appl. No.: 14/613,644

(22) Filed: Feb. 4, 2015

(65) Prior Publication Data

US 2015/0223695 A1   Aug. 13, 2015

Related U.S. Application Data

(60) Provisional application No. 61/937,158, filed on Feb. 7, 2014.

(51) Int. Cl.
*A61B 5/00* (2006.01)

(52) U.S. Cl.
CPC .......... *A61B 5/0066* (2013.01); *A61B 5/0079* (2013.01); *A61B 5/0088* (2013.01); *A61B 5/441* (2013.01); *A61B 5/7425* (2013.01)

(58) Field of Classification Search
CPC .... A61B 5/0066; A61B 5/0079; A61B 5/0088; A61B 5/7425
USPC ......................................................... 356/479
See application file for complete search history.

(56) References Cited

U.S. PATENT DOCUMENTS

| | | | |
|---|---|---|---|
| 2007/0040033 A1* | 2/2007 | Rosenberg | A47G 1/02 235/462.36 |
| 2007/0081166 A1* | 4/2007 | Brown | A61B 3/1005 356/479 |
| 2011/0299034 A1* | 12/2011 | Walsh | A61B 3/102 351/206 |

* cited by examiner

*Primary Examiner* — Jonathan Hansen
(74) *Attorney, Agent, or Firm* — Foley & Lardner LLP

(57) ABSTRACT

Diagnostic devices are generally described. In an example, an improved diagnostic device includes a display, a camera, a diagnostic probe, and a control unit. The display includes an aperture. The camera is configured to capture an image of a patient through the aperture. The diagnostic probe is configured to perform measurements of an area of interest of the patient through the aperture. The control unit is configured to analyze the measurements of the diagnostic probe and cause the display to present the image of the patient and results of the measurements on the image of the patient.

15 Claims, 3 Drawing Sheets

SELF-OPERATED HEALTH MONITORING DEVICE

CROSS-REFERENCE TO RELATED PATENT APPLICATIONS

This application claims priority from U.S. Provisional Application No. 61/937,158, filed Feb. 7, 2014, which is incorporated herein by reference in its entirety.

BACKGROUND

The following description is provided to assist the understanding of the reader. None of the information provided or references cited is admitted to be prior art.

Frequent monitoring of a person's body using imaging device is useful for early diagnosis and prevention of many diseases. Imaging devices such as optical coherence tomography (OCT) are useful tools for such applications. However, traditional diagnostic imaging devices require an operator separate from the patient to operate the imaging device (including, for example, a probe for performing measurements and a display for showing results to the patient).

SUMMARY

The present technology provides an improved diagnostic device that includes a display, a camera, a diagnostic probe, and a control unit. The display includes an aperture. The camera is configured to capture an image of a patient through the aperture. The diagnostic probe is configured to perform measurements of an area of interest of the patient through the aperture. The control unit is configured to analyze the measurements of the diagnostic probe and cause the display to present the image of the patient and results of the measurements on the image of the patient.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

DETAILED DESCRIPTION

Figure 1:
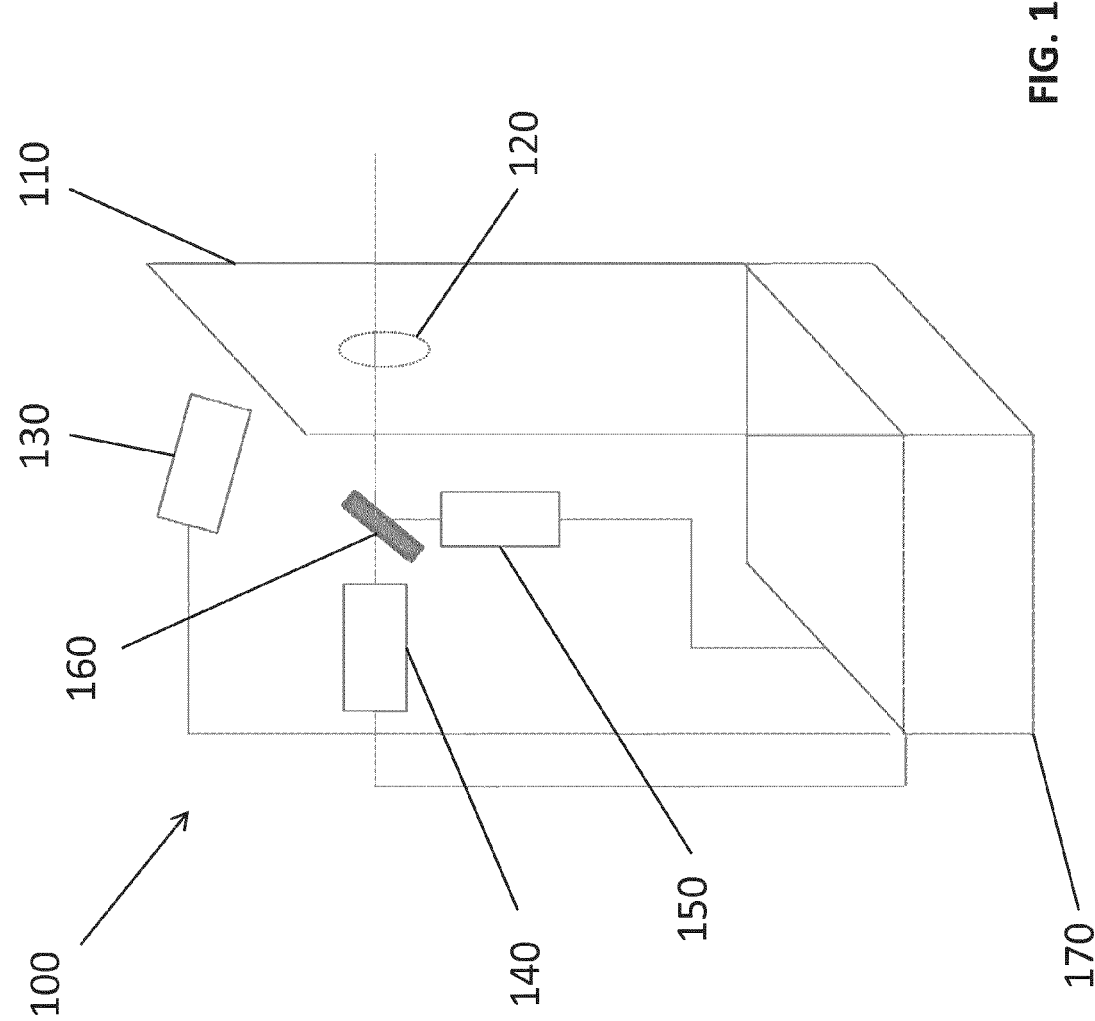
FIG. 1 depicts a self-operated imaging device in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein is an optical coherence tomography (OCT) imaging device that may be operated by a patient on which the imaging is being performed. In this way, a patient may perform imaging and diagnostic operations without the aid of another person, thereby enabling a patient to perform the imaging at a convenient time and location. In accordance with an embodiment, an OCT imaging device includes a display that acts as a mirror and that is combined with a measurement probe. The combination of the display and mirror enable a patient to self-align the probe with a sample (e.g., an eye) and to operate the diagnostic device and view the results on the same surface of the display.

FIG. 1 depicts a self-operated imaging device 100 in accordance with an illustrative embodiment. Self-operated imaging device 100 includes a display 110 having an aperture 120 formed therein. In alternative embodiments, display 110 may have multiple apertures 120 according to the imaging requirements or options of the device. Self-operated imaging device 100 further includes a camera 140, a diagnostic probe 150, and a combiner mirror 160 configured to utilize aperture 120. Self-operated imaging device 100 also includes a control unit 170 configured to receive information from camera 140 and diagnostic probe 150 and perform various processing functions. In an embodiment, self-operating imaging device 100 also includes a second camera 130 that may be configured to capture a different view than camera 140. For example, camera 130 may be configured to capture a wider or perspective view that encompasses a larger field of view than camera 140.

Figure 2:
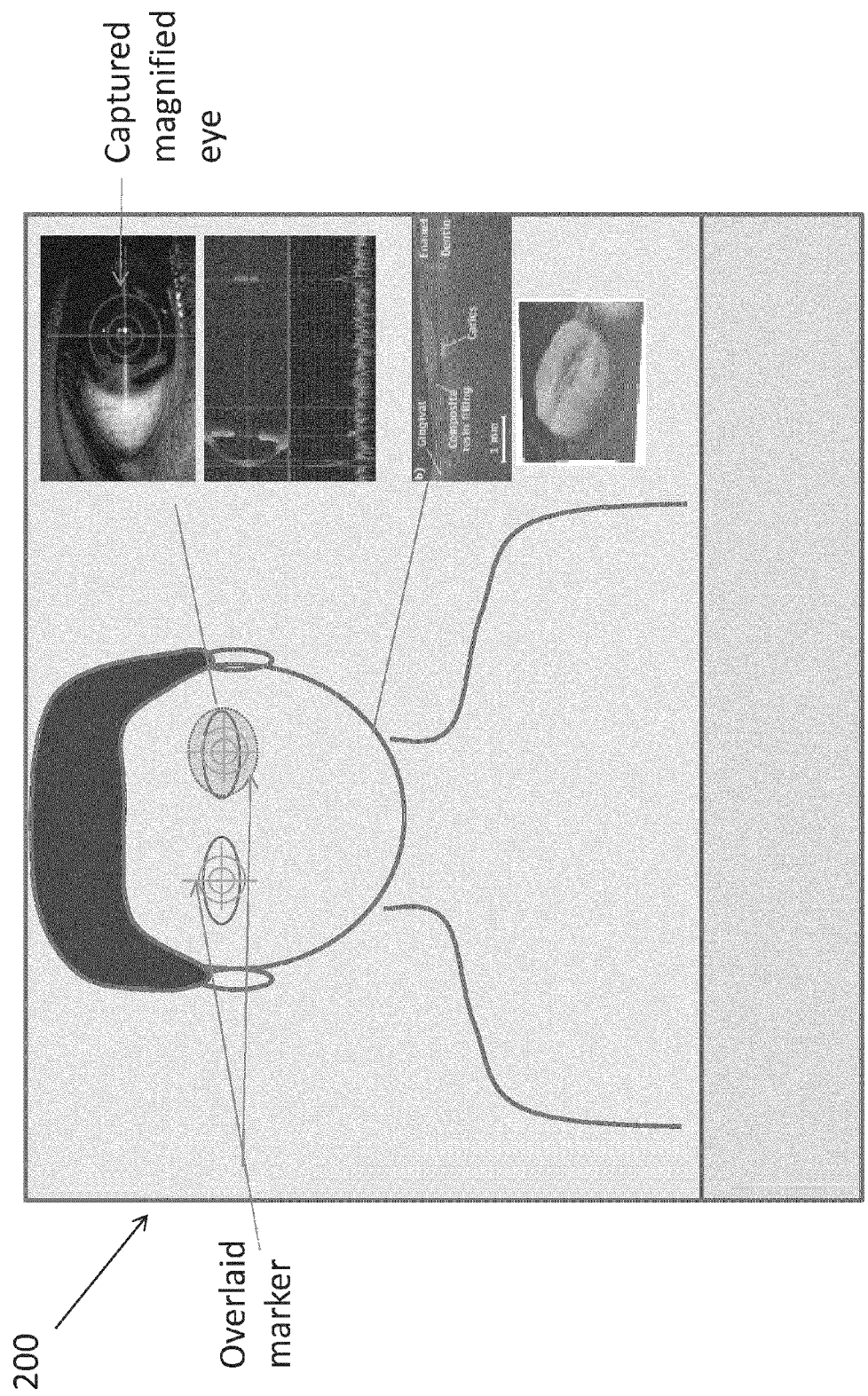
FIG. 2 depicts an example display in accordance with an illustrative embodiment.

In an embodiment, display 110 includes a screen that displays a mirror image of a patient together with test or diagnostic results. Display 110 may include a liquid crystal display (LCD), a light emitting diode (LED) display, a projection panel display, or any other suitable display known to those of skill in the art. In an embodiment, to display the mirror image of the patient, right and left sides of an image captured by the camera are inverted and a size of the image is adjusted to correspond to an actual size of the patient. Display 110 may also be configured to display guide instructions or markers to aid the patient in aligning the area of interest with aperture 120. In an embodiment, display 110 is configured to present an alignment marker on the screen indicating where a patient should align the area of interest relative to display 110. For example, display 110 may overlay the alignment mark on top of a mirror image of the patient that includes a target in which the user is to align the area of interest, e.g., an eye. FIG. 2 discussed below shows an example of such an overlaid alignment marker. In an embodiment, the alignment marker includes a circle and cross lines on display 110. The alignment marker represents a desired location for the positioning of the area of interest of the patient at which diagnostic probe 150 will be properly aligned with and able to analyze the area of interest.

Display 110 may also include a touch screen interface or other user interface known to those of skill in the art. In an embodiment, the user interface allows the patient or user to commence, modify, customize, etc., measurements performed by self-operated imaging device 100. In addition, the user interface may allow the patient to customize and revise results of the measurements. FIG. 2 depicts a display 200 in accordance with an illustrative embodiment. Display 200 depicts a mirror image of a patient including test information/results for imaging of the eye and imaging of the mouth/teeth. Display 200 includes overlaid alignment markers presented on the screen to aid the patient in aligning the area of interest, e.g., the eyes, with diagnostic probe 150. The test information/results presented on display 200 include an image of the captured magnified eye as well as other results.

Camera 140 is configured to capture an image of the patient through aperture 120. In an embodiment, camera 140 may include a charge-coupled device (CCD) imaging device, a complementary metal-oxide-semiconductor (CMOS) imaging device, or any other suitable imaging device known to those of skill in the art. In still another embodiment, camera 140 may include zoom functions that allow a user or patient to selectively zoom in or zoom out of an area of interest. Camera 140 may also include a reinvert function that allows a user or patient to selectively reinvert the right and left sides of the image to show an actual image (as opposed to a mirror image) of the patient or user. In another embodiment, camera 140 may capture live real-time video of the patient or user and/or may capture a snap shot of the patient or user or an area of interest of the patient or user. In still additional embodiments, self-operated imaging device 100 may include multiple cameras 140 that may be configured to capture images via one or more apertures 120. The multiple cameras 140 may each be directed to a same area of interest or may each be directed to different areas of interest. For example, a first camera may be configured to capture a specific area of interest (e.g., an eye) and a second camera may be configured to capture a wider area view (e.g., the entire head or the entire patient). The first and second cameras may capture their respective images through a same or different apertures in the display.

Diagnostic probe 150 is configured to obtain measurements and/or images of an area of interest (e.g., a selected body part) of the patient via aperture 120. In an embodiment, diagnostic probe 150 may include an optical coherence tomography (OCT) probe configured to analyze a body part (e.g., eye, tooth, skin, etc.). In alternative embodiments, diagnostic probe 150 may include measurement devices other than an OCT probe as known to those of skill in the art. In alternative embodiments, self-operated imaging device 100 may include multiple same or different diagnostic probes 150 configured to perform measurements through one or more apertures 120.

Combiner mirror 160 is configured to allow camera 140 and diagnostic probe 150 to use the same aperture 120 for imaging the patient. As such, camera 140 and diagnostic probe 150 may share a same optical axis passing through aperture 120. In an embodiment, light or signals from or to camera 140 are transmitted directly through combiner mirror 160 and to aperture 120 while light or signals to or from diagnostic probe 150 are reflected by combiner mirror 160 through aperture 120. In an alternative embodiment, the positions of camera 140 and diagnostic probe 150 may be swapped so that light or signals from or to diagnostic probe 150 are transmitted directly through combiner mirror 160 and to aperture 120 while light or signals to or from camera 140 are reflected by combiner mirror 160 through aperture 120.

Control unit 170 is configured to receive information from camera 140 and diagnostic probe 150 and perform various processing functions for performing measurements and displaying images and results on display 110. Control unit 170 includes a memory and processor as known to those of skill in the art. The processor is configured to execute computer-readable instructions stored in the memory to perform the various processing functions. In an embodiment, control unit 170 causes display 110 to display an image of the patient or an area of interest of the patient on the display in accordance with data received from camera 140. The display of the image of the patient may be a mirror image of the patient together with instructions or markers to aid the patient in aligning a body part with aperture 120 to facilitate analysis by diagnostic probe 150. Control unit 170 also causes display 110 to display measurements and diagnoses in accordance with data received from diagnostic probe 150. Control unit 170 is further configured to receive instructions from the patient or user via an interface on display 110 and to implement operations in accordance with those instructions.

In an embodiment, control unit 170 is configured to store measurement and/or diagnosis data about the patient or an analyzed body part in its memory (or in an external database) to compare and monitor progress or healing of a condition or disease. Control unit 170 may also include an external link for uploading or downloading data to external devices or resources. For example, control unit 170 may be configured to connect with external resources such as hospitals, doctors, or networks for consulting or remote diagnosis. Such connections may be via the Internet, an intranet, or any other networks known to those of skill in the art.

Figure 3:
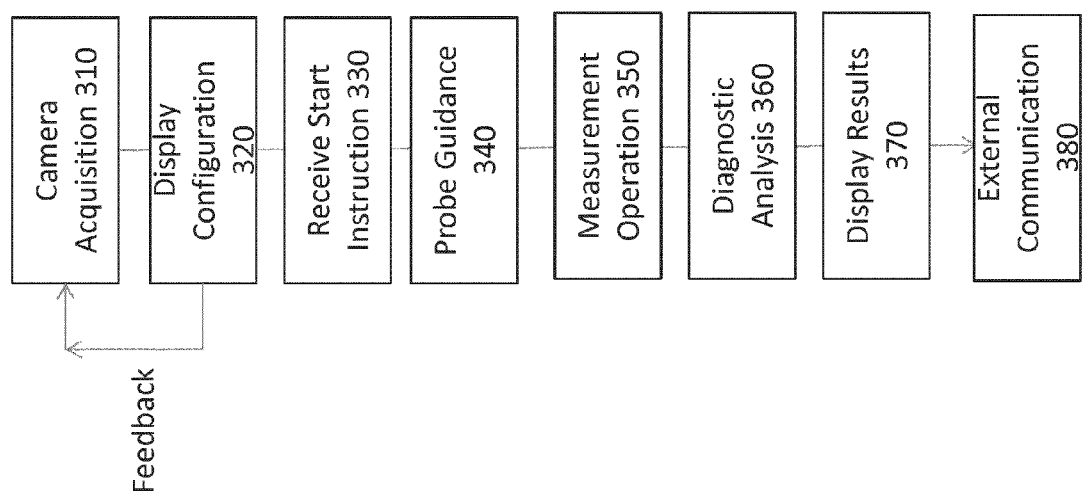
FIG. 3 depicts a flow diagram showing operation of a self-operated imaging device in accordance with an illustrative embodiment.

FIG. 3 depicts a flow diagram showing operation of a self-operated imaging device in accordance with an illustrative embodiment. In a camera acquisition operation 310, a camera of the self-operated imaging device acquires an image of a patient via an aperture in the self-operated imaging device. Camera acquisition operation 310 may include the performance of various camera configuration operations. For example, the camera may perform one or more auto focus operations, distance detection operations, zoom operations, or any other camera configuration options known to those of skill in the art to obtain a high quality image of the patient or of an area of interest of the patient.

In a display configuration operation 320, a display of the self-operated imaging device is configured so that a high quality image of the patient or the area of interest of the patient is shown on the display. Configuration of the display may include automatic inversion of a mirror image to an actual image (or vice versa), a size adjustment of the area of interest shown on the display, or any other display configuration operations known to those of skill in the art. Display configuration operations may be prompted by patient inputs via a user interface or may automatically be performed by the self-operated imaging device. In an embodiment, display configuration operations may provide feedback to the camera for modification of the configuration parameters of the camera. For example, adjustment of the display size on the display may prompt zoom parameter changes to the camera.

In a receive start instruction operation 330, an instruction is received by the self-operated imaging device to commence measurements with a diagnostic probe. In an embodiment, the patient or user may initiate the start instructions via a user interface on the display or in another location. In another embodiment, the self-operated imaging device may automatically commence measurements, e.g., a set time after completion of display configuration operation 320.

In a probe guidance operation 340, a diagnostic probe is aligned and configured for measurement of the area of interest of the patient (e.g., eye, skin, teeth, etc.). In an embodiment, a guide marker is overlaid on the display of the area of interest of the patient.

In a measurement operation 350, the self-operated imaging device performs measurements of the area of interest of the patient via the diagnostic probe. In an embodiment, the diagnostic probe is an OCT imaging device configured to measure diagnostic information of an eye via optical reflections. In alternative embodiments, the diagnostic probe may include one or more other measurement devices known to those of skill in the art.

In a diagnostic analysis operation 360, a control unit of the self-operated imaging device receives data regarding the measurement operation 350 from the diagnostic probe and performs diagnostic analysis of the measurements. In a display results operation 370, results of the diagnostic analysis are displayed on the display of the self-operated imaging device. In an embodiment, the results are overlaid on an image of the patient on the display of the self-operated imaging device.

In an external communication operation 380, the self-operated imaging device connects with external resources such as hospitals, doctors, or networks for consulting or remote diagnosis. Such connections may be via the Internet, an intranet, a wireless network, a local area network, a wired network, or any other networks known to those of skill in the art. In an embodiment, the self-operated imaging device may be automatically connected to a predetermined external resource and may automatically communicate the results of the diagnostic analysis to the external resource. In another embodiment, connections with external resources may be manually initiated by the patient in response to inputs provided by the patient via an interface on the display of the self-operated imaging device. In this way, the patient may select whether consultation is desired and may select the particular external resource to be consulted.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

What is claimed is:

1. A diagnostic device comprising:
    a display comprising an aperture;
    a camera configured to capture an image of a patient through the aperture;
    a diagnostic probe configured to perform measurements of an area of interest of the patient through the aperture; and
    a control unit configured to:
        analyze the measurements of the diagnostic probe; and
        cause the display to present the image of the patient and results of the measurements on the image of the patient.

2. The diagnostic device of claim 1, wherein the control unit is configured to cause the display to present a mirror image of the patient on the display.

3. The diagnostic device of claim 2, wherein causing the display to present the mirror image comprises inverting right and left sides of an image captured by the camera and adjusting a size of the image to correspond to an actual size of the patient.

4. The diagnostic device of claim 1, wherein the camera is configured to capture video of the patient in real time.

5. The diagnostic device of claim 1, wherein the camera is configured to capture a still image of the patient or of the area of interest of the patient.

6. The diagnostic device of claim 1, wherein the control unit is configured to cause the camera to perform a zoom function in response to adjusting a size of the image to correspond to an actual size of the patient for presentation of a mirror image of the patient on the display.

7. The diagnostic device of claim 1, wherein the diagnostic probe comprises an optical coherence tomography (OCT) imaging device, and wherein the control unit is configured to cause the display to present information regarding a cross section and related diagnostic information of an eye obtained by the OCT imaging device.

8. The diagnostic device of claim 1, wherein display comprises a plurality of apertures, and wherein the diagnostic device further comprises a plurality of cameras and diagnostic probes that correspond to respective apertures of the plurality of apertures.

9. The diagnostic device of claim 1, further comprising a combining mirror, and wherein the camera and the diagnostic probe share a same optical axis with the combining mirror.

10. The diagnostic device of claim 1, further comprising a first camera configured to capture a view of a specific body part of the patient and a second camera configured to capture a perspective view of the patient that encompasses a wide area than the first camera.

11. The diagnostic device of claim 1, wherein the display comprises a touch screen interface configured to receive inputs from the patient.

12. The diagnostic device of claim 1, further comprising a communication component configured to establish communication with external resources.

13. The diagnostic device of claim 1, wherein the diagnostic probe is configured to produce OCT images of an eye, dental tissue, and skin.

14. The diagnostic device of claim 1, wherein the camera is a separate component from the diagnostic probe.

15. The diagnostic device of claim 1, wherein the display further comprises a display area that surrounds the aperture.

\* \* \* \* \*